United States Patent [19]

Keogh et al.

[11] Patent Number: 5,509,932
[45] Date of Patent: Apr. 23, 1996

[54] FIXED TISSUE MEDICAL DEVICES COMPRISING ALBUMIN-BINDING DYES

[76] Inventors: James R. Keogh, 1201 Frank Ct., Maplewood, Minn. 55109; David A. Pearson, 7717 Beard Ave. North, Brooklyn Park, Minn. 55443; John W. Eaton, 76 Bulson Rd., Troy, N.Y. 12180

[21] Appl. No.: 44,846

[22] Filed: Apr. 8, 1993

[51] Int. Cl.$^6$ ..................... A61F 2/02
[52] U.S. Cl. ............. 623/11; 623/2; 604/266
[58] Field of Search ............. 623/1, 2, 11, 12; 600/36; 604/266; 606/191

[56] References Cited

U.S. PATENT DOCUMENTS

| | | |
|---|---|---|
| 4,323,358 | 4/1982 | Lentz . |
| 4,378,224 | 3/1983 | Nimni et al. . |
| 4,402,697 | 9/1983 | Pollock et al. . |
| 4,405,327 | 9/1983 | Pollock . |
| 4,481,009 | 11/1984 | Nashef . |
| 4,553,974 | 11/1985 | Dewanjee . |
| 4,647,283 | 3/1987 | Carpentier et al. . |
| 4,648,881 | 3/1987 | Carpentier . |
| 4,729,139 | 3/1988 | Nashef . |
| 4,753,652 | 6/1988 | Langer . |
| 4,770,665 | 9/1988 | Nashef . |
| 4,838,888 | 6/1989 | Nashef . |
| 4,885,005 | 12/1989 | Nashef . |
| 4,976,733 | 12/1990 | Giardot . |
| 4,979,959 | 12/1990 | Guire ......................... 623/1 |
| 5,002,566 | 3/1991 | Carpentier . |
| 5,055,316 | 10/1991 | Hoffman et al. ............. 427/2 |
| 5,073,171 | 12/1991 | Eaton . |
| 5,217,492 | 6/1993 | Guire et al. ................ 623/1 |

OTHER PUBLICATIONS

Dean et al, Protein Purification, J. Chromat., vol. 165, pp. 301–319.

*Primary Examiner*—Paul B. Prebilic
*Attorney, Agent, or Firm*—Daniel W. Latham; Harold R. Patton

[57] ABSTRACT

An implantable medical device is provided which comprises a fixed tissue incorporating an amount of an albumin-binding dye effective to form a coating of endogenous albumin on said device when the device is in contact with a physiological fluid containing albumin. These albumin-binding dyes have been found to significantly reduce calcification when incorporated in tissue heart valves. A method of increasing the albumin-binding ability of an implantable medical device is also provided.

32 Claims, 2 Drawing Sheets

FIXED TISSUE MEDICAL DEVICES COMPRISING ALBUMIN-BINDING DYES

FIELD OF THE INVENTION

The present invention relates generally to implantable medical devices made from fixed tissue which have increased ability to bind albumin from a physiological fluid containing albumin, and more particularly to such devices as tissue heart valves and other intravascular prosthetic devices which possess improved anticalcification and antithrombogenic properties.

BACKGROUND OF THE INVENTION

A. Effects of Implantable Devices

Implantable medical devices made of various materials may cause a number of iatrogenic effects in patients. First, implantable medical devices can serve as foci for infection of the body. Infection is promoted by the tendency of bacterial organisms to adhere to the surfaces of implantable devices and, while adherent, to resist destruction by phagocytic cells that normally would destroy these organisms.

Second, implantable devices also tend to serve as a nidus, or focus, for the formation of thrombi (blood clots). This is because the surfaces of the implanted materials may activate non-cellular plasma clotting factors. Furthermore, platelets which adhere to the surfaces of these materials become activated and form thrombi. The procoagulant activities of many materials can prevent their use in vivo, or can greatly diminish their useful lifetime. In addition, even materials which are chemically inert may act as foci for the formation of inflammatory lesions such as granulomas, resulting, in many cases, in the necessity for removal of the implanted device.

B. Calcification of Animal Tissue Implants

Aldehydes such as formaldehyde and especially glutaraldehyde are commonly used to control the physical and biological properties of a variety of animal tissue derived materials such as tissue heart valves and other tissue-derived implantable devices. It is well established that pre-treatment of protein-containing biological tissue material with aldehydes causes a cross-linking reaction with the amine groups in the protein which reduces the solubility, antigenicity, and biogradation of the treated material. However, it is also well-known that such implants must be treated to avoid problems after implantation, for example, excessive mineralization or calcification and rejection by the body's immune system.

Numerous treatments for preventing calcification and improving the stability of prosthetic devices made from natural tissue have therefore been proposed.

In U.S. Pat. No. 5,002,566 issued to Carpentier et al., a calcification resistant bioprosthetic implant is described which is made from tanned biological material which has been impregnated with a calcification-mitigating amount of a ferric and/or stannic salt.

In U.S. Pat. No. 4,976,733 issued to Girardot, a method for retarding or preventing the calcification of a prosthesis implanted in a mammal is described in which before implantation an effective amount of an anticalcification agent is coupled to the prosthesis in the form of an aliphatic carboxylic acid. For a natural tissue prosthesis, such coupling may be to an aldehyde group of glutaraldehyde in which the tissue is pre-soaked.

In U.S. Pat. No. 4,885,005 issued to Hashef et al., a process for the preparation of implantable biological tissue is described, and in particular bioprosthetic heart valves, which are prone to calcification after implantation in which the process includes the treatment of tissue with an effective amount of a surfactant to reduce calcification of the implanted tissue.

In U.S. Pat. No. 4,838,888 issued to Nashef, a process for treating biological tissue prior to implantation to mitigate the calcification of the tissue following implantation is described, incorporating acetylsalicylic acid into the tissue in an amount effective to reduce calcification of the tissue after it is implanted.

In U.S. Pat. No. 4,770,665 issued to Nashef, a process for the preparation of implantable biological tissue is described wherein elastomeric copolymers are incorporated into the tissue in an amount sufficient to increase the durability of the tissue as well as to reduce calcification of the tissue upon implantation.

In U.S. Pat. No. 4,753,652 issued to Langer et al., a biomaterial implant is described into which is incorporated a sustained release polymer containing an anticalcium agent (e.g., ethanehydroxydiphosphonate (EHDP), EDTA, or aminopropanediphosphonate (APDP).

In U.S. Pat. No. 4,729,139 issued to Nashef, a process for selectively incorporating biocompatible polymers in the interstices of implantable biological tissue is described in which the outer surface of the tissue is left substantially free of bonded polymer. The process involves covalently binding a monomer to the tissue, contacting the tissue with a free-radical initiator, then contacting the tissue with a solution containing a second monomer and a free-radical scavenger, thereby promoting selective polymerization of the second monomer with the portion of covalently-bound first monomer which is located in the interstices of the tissue.

In U.S. Pat. No. 4,648,881 and 4,647,283 issued to Carpentier et al., a process for the preparation of implantable biological tissue is described which has been found effective in reducing calcification of the implanted tissue in which the tissue is contacted with a phosphate-deficient solution or a calcium-binding competing divalent cation.

In U.S. Pat. No. 4,553,974 issued to Dewangee, a process for treatment of collagenous tissue used in a prosthetic implant (e.g., a heart valve) is described in which a surfactant, an anti-calcification agent (i.e., amino diphosphonates) and, optionally, a stabilizing agent are used to prevent calcification.

In U.S. Pat. No. 4,481,009 issued to Nashef, a process is disclosed for the preparation of implantable biological tissue which includes the incorporation of biocompatible polymers into the tissue in an amount effective in reducing calcification of the implanted tissue (e.g., the covalent immobilization of monomers onto the biological tissue followed by further polymerization).

In U.S. Pat. No. 4,405,327 issued to Pollock, natural tissues are fixed with a tanning solution such as glutaraldehyde and treated with a solution of a water soluble quaternary ammonium salt such as dodecyltrimethylammonium chloride to inhibit calcification of the tissue after implantation.

In U.S. Pat. No. 4,402,697 issued to Pollock et al., natural tissues fixed with a tanning solution such glutaraldehyde are treated with a solution of a water soluble phosphate ester such as sodium dodecyl hydrogen phosphate to inhibit calcification of the tissue after implantation.

In U.S. Pat. No. 4,378,224 issued to Nimni et al., a coating and integral treating for improving the calcification of heart valves is described with covalently attached calcification inhibitors (e.g., natural protein polysaccharides, such as chondroitin sulfates and hyaluronate; diphosphonates, phosphoproteins, dyes, such as alzarin red S and methylene blue, and other polyanions may be used).

In U.S. Pat. No. 4,323,358 issued to Lentz et al., treatment of a glutaraldehyde-fixed animal tissue with a solution of a water-soluble salt of a sulfated higher aliphatic alcohol is disclosed, such as sodium dodecyl sulfate, to inhibit calcification of the tissue after implantation.

However, there is still a need for methods to render the surfaces of implantable tissue-derived materials less thrombogenic, less pro-inflammatory and less prone to calcification.

C. Albumin Selectivity

Albumin is the predominant plasma protein, readily soluble in water and in constant contact with the luminal surface of the vascular endothelium. The vascular endothelium itself imparts several desirable characteristics to the walls of blood vessels, including diminished tendency to promote coagulation, reduced attractiveness for inflammatory, phagocytic cells, and increased ability to resist colonization by pathogenic bacteria.

In its normal configuration, albumin does not promote clotting nor attract inflammatory cells. It has been found to be desirable to coat the surfaces of medical devices with albumin, thereby imparting these same characteristics to the surface of biomaterial. In U.S. Pat. No. 5,073,171 issued to Eaton, a biocompatible prosthetic device is described in which a synthetic material from which it is made incorporates an amount of an albumin-binding dye effective to form a coating of endogenous albumin on the device when the device is in contact with a physiological fluid containing albumin.

SUMMARY OF THE INVENTION

In the present invention we have found that implantable medical devices comprising fixed animal tissue which incorporate certain dyes which are disclosed herein that have a high and selective affinity for albumin when exposed to a fluid containing albumin, such as a physiological fluid, possess improved anti-thrombogenic and anti-calcification properties. Accordingly, the present invention provides an implantable medical device comprising fixed animal tissue incorporating an amount of an albumin-binding dye effective to form a coating of endogenous albumin on the device when the device is in contact with a physiological fluid containing albumin. The albumin-binding dye preferably comprises an aromatic albumin-binding dye which comprises a diazo dye, a sulfonic acid dye, or the physiologically-acceptable salts thereof. In a preferred embodiment of the invention, the albumin-binding dye is present in a conjugate also comprising a physiologically-acceptable, high molecular weight, water-soluble polysaccharide such as dextran.

In another preferred embodiment of the invention, a fixed tissue implantable medical device is provided which comprises the dye/polymer conjugate in an amount effective to bind albumin to the surface of the fixed tissue. An especially preferred fixed tissue device is a prosthetic heart valve.

The present invention further provides a method of increasing the albumin-finding ability of a fixed tissue implantable medical device.

Advantageously, tissue medical devices incorporating the albumin-binding fixed dye are less thrombogenic and have substantially reduced susceptibility to calcification than devices made without the albumin-binding dye.

As used herein, the term "endogenous albumin" refers to the albumin which is normally present in a physiological fluid, such as the human serum albumin present in human blood. However, fixed tissue implantable medical device with incorporated albumin-binding dye can also bind albumin from synthetic solutions, thereby precoating the device with albumin prior to its introduction into a body cavity.

DETAILED DESCRIPTION OF THE INVENTION

A. Implantable Medical Device

Figure 1:
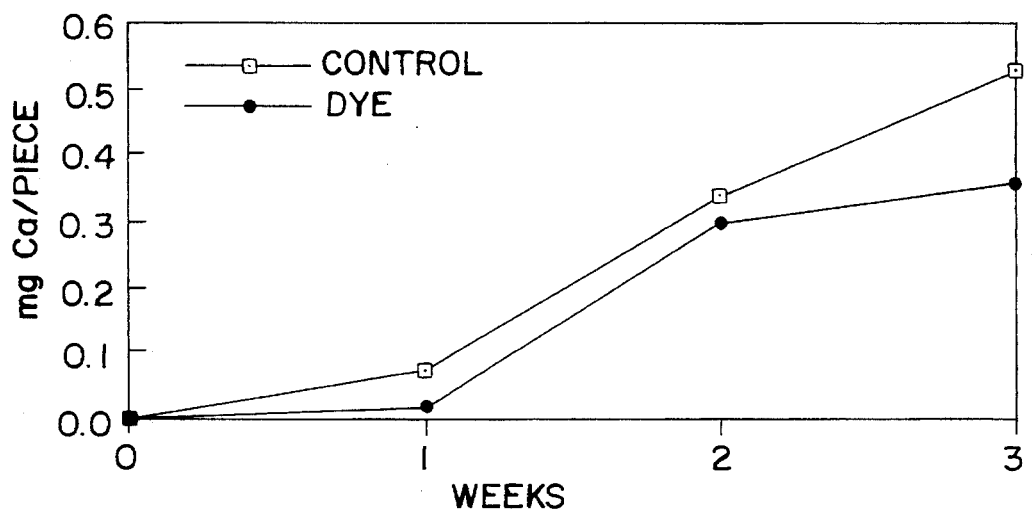
FIG. 1 is a graph comparing the calcification (calcium content) of control tissue with that of dye-treated tissue according to the present invention as set forth in Example 1.

The present invention provides a fixed tissue medical device which is implantable in humans or animals. As used herein, the word "implantable" means any application in which the device is intended to be implanted in a human or animal body or applied to any unhealed would on a human or animal body. A "medical device" is intended to mean any structure or mechanism intended for use in the diagnosis of disease or other condition or in the cure, mitigation or prevention of disease. Examples of implantable medical devices which the present invention is intended to encompass include replacement cardiovascular material such as heart valves and blood vessels, suture material, replacement connective tissue, graft material for oral surgery, artificial vein, biomembrane material for repair of dural defects and the like.

B. Fixed Tissue

The fixed tissue of the present invention comprises animal tissue fixed with a cross-linking agent. The animal tissue of the present invention can be any proteinaceous animal tissue such as heart valves, blood vessels, ureters, tendons, ligaments, pericardium, skin, and proteinaceous products from animal sources such as collagen. The animal tissue can be in the form of whole animal tissue such as whole heart valves, arteries, veins and the like or in the form of a liquid or gel or in solid shapes such as sheets, sponges, fibers or the like. A wide variety of proteinaceous animal tissue sources could be used including the commonly used porcine or bovine sources.

The animal tissue is fixed with an aldehyde. By "fixed" we mean cross-linked by a reaction between the aldehyde and protein amine components to stabilize a protein matrix such as that found in collagen. The aldehyde used can be any aldehyde suitable for fixing tissue of the desired type such as glutaraldehyde, glyoxal, malonaldehyde, succinaldehyde, adipaldehyde, dialdehyde starch, formaldehyde, acrolein and acetaldehyde. Preferably, the aldehyde is glutaraldehyde, an aldehyde commonly used in the fixation of implantable medical products made from animal tissue. The particular methods and apparatus used to fix tissue are well known to those skilled in the art. Preferably, the fixed tissue used in the present invention is also treated with a reducing agent to stabilize the labile cross-link provided by the treatment with aldehyde. Reducing agents such as sodium borohydride, sodium cyanoborohydride and amine boranes could be used with treatment with cyanoborohydride most preferred.

C. Aromatic Albumin-Binding Dyes

The implantable medical device of the present invention comprises an albumin-binding dye. Preferably the albumin-binding dye comprises an aromatic albumin-binding dye. The aromatic albumin-binding dye preferably comprises a diazo dye; a physiologically-acceptable alkali metal salt, alkaline earth metal salt, or amine salt of said diazo dye; a sulfonic acid dye; a physiologically-acceptable alkali metal salt, alkaline earth metal salt, or amine salt of said sulfonic acid dye; or mixtures thereof.

Aromatic albumin-binding dyes particularly useful in the present invention include Reactive Blue 2 (1-Amino-4[[4-[[4-chloro-6-[[3(or 4)-sulfophenyl]amino]-1,3,5-triazin-2-yl] amino]-3-sulfophenyl]amino]-9,10-dihydro-9,10-dioxo-2-anthracenesulfonic acid), available from Sigma Chemical Company, St. Louis, Mo.; Evans Blue (6,6'-(3,3'-Diamethyl [1,1'-biphenyl]-4,4'diyl)bis(azo)]bis[4-amino-5-hydroxy-1,3-naphthalene disulfonic acid] tetrasodium salt), (Sigma); Trypan Blue (3,3'-[3,3'-Dimethyl[1,1'-biphenyl]- 4,4'diyl) bis(azo)]bis[5-amino-4 hydroxy-2,7-naphthalene disulfonic acid] tetrasodium salt), (Sigma); Bromcresol Green (4,4'-(3H-2,1-Benzoxathiol-3-ylidene)bis[2,6-dibromo- 3-methylphenol]S,S-dioxide), (Sigma); Bromcresol Purple (4,4'-(3H-2,1-benzoxathiol-3-ylidene)bis[2-bromo-6-methylphenol] S,S-dioxide), (Sigma); Methyl Orange (4-[[(4-dimethylamino) phenyl]azo]benzene-sulfonic acid sodium salt), (Sigma);2-(4'-hydroxyazobenzene)benzoic acid, (Sigma); Procion red H-E 3B, as disclosed by Dean and Watson, *J. Chromatography,* 165:301–319 (1979), incorporated herein by reference; and mixtures thereof.

The albumin-binding dye is preferably integrally contained within and throughout the implantable medical device as on its surface. Alternatively, the dye may be chemically bound to the surface of the implantable medical device, thereby modifying only the surface of the implant.

If the dye is to be chemically bound to the device surface, available functional groups in the dye may be used to link the dye to the surface. An appropriate linking agent is chosen based on its compatibility with the available reactive functional group. It is important, however, that the regions of the dye containing sulfonate groups are left free to interact with albumin.

D. Dye/Polymer Conjugate

A preferred embodiment of providing implantable medical devices with albumin-binding dyes determines the way in which the albumin associates with the dye. In order to bind, but not to substantially denature the albumin, it is preferable to situate or space the dye some distance from the surface other polymeric material. Therefore, a preferred embodiment of the present invention includes a polymeric body comprising a conjugate comprising a physiologically acceptable high molecular weight, water-soluble polymer such as a polysaccharide or a polypeptide comprising at least one albumin-binding dye, as defined above. A water-soluble polysaccharide is utilized in order to maximize the extent of surface exposure of the molecules of the albumin-binding dye and their ability to subsequently interact with albumin.

A commercially available polysaccharide suitable for use in the present invention is dextran, available from Sigma Chemical Company, St. Louis, Mo. A dextran may be generally defined as a polysaccharide containing a backbone of D-glucose units linked predominantly α-D(1→6). Dextran with an average molecular weight of 40,000, designated as "Dextran 40", is commercially available as Gentran 40® from Baxter Travenol Laboratories, Deerfield, Ill.; as LMD® from Abbott Laboratories, North Chicago, Ill.; and as Rheomacrodex from Pharmacia Fine Chemicals, Uppsala, Sweden. Dextran with an average molecular weight of 75,000, designated "Dextran 75", is commercially available as Gentran 75® from Baxter Travenol Laboratories, Deerfield, Ill.; and as Macrodex from Pharmacia Fine Chemicals, Uppsala, Sweden.

A commercially-available, pre-mixed form of the conjugate of the present invention is marketed under the designation Blue Dextran by Pharmacia Fine Chemicals, Uppsala, Sweden, and is also commercially available under the same tradename from Sigma Chemical Company, St. Louis, Mo. Blue Dextran is prepared from dextran with an average molecular weight of about $2\times10^6$ and incorporates approximately 0.1 mmol of the dye Reactive Blue 2 per gram of dextran.

Other biocompatible, water-soluble polysaccharides which can be conjugated to albumin-binding dyes are also useful in the present invention. These include alginates, modified celluoses, modified starches, and the like.

In a preferred embodiment of the present invention, the dye/polymer conjugate is incorporated into the fixed tissue, as defined above, thereby presenting a high concentration of the desired dye at the surface of the fixed tissue. A substantial number of the total dye molecules are exposed to the extent that they can bind albumin without substantial denaturation of the bound protein.

The precise ratios of dye/polymer conjugate to solvent to fixed tissue which are used depend on a number of considerations, including the solubility characteristics of the dye preparation and the fixed tissue of choice. Preferably, the albumin-binding fixed tissue of the present invention will be prepared from a dye/polymer conjugate, fixed tissue, and a solvent, present respectively in an initial weight ratio of about 1:0.5–2:20, more preferably about 1:0.25–4:40, and most preferably about 1:0.25–6:60.

An advantage of this preferred embodiment of the present invention is that the dye/polymer conjugate in the finished device is durable and pervasive. Thus, implantable medical devices prepared as described herein will retain modified surface characteristics for prolonged periods during in vivo implantation. Furthermore, because the dye permeates the entire material (rather than just being present on the surface), erosion of the original surface will not destroy the unique albumin-binding properties of the fixed tissue.

Alternatively, the dye/polymer conjugate may be chemically or ionically bound to the surface of the fixed tissue, thereby modifying only the surface of the implant. This can be accomplished by dipping, spraying or brushing a solution of the conjugate onto the surface of the fixed tissue device and removing the solvent under suitable conditions. Additionally, the albumin-binding dye or its conjugates may be chemically reacted with monomers or polymers of implant materials (such as the cross-links imparted by the aldehyde treatment) to produce a final product in which the dye is an integral part of the finished polymer.

E. Physiological Fluids

The present invention promotes the binding of albumin to an implantable medical device when the device is in contact with a physiological fluid containing albumin. Such contact may occur in vitro or ex vivo. Examples of the physiological fluids with which the prosthetic device of the present invention may come into contact include blood, lymph, saliva, urine, tears, and cerebro-spinal fluid.

While we do not wish to be bound by theory, the bound albumin-binding dye is believed to selectively and reversibly bind albumin and thereby form a renewable albumin coating ont eh fixed tissue. The albumin would then scavenge any free calcium deposited on the fixed tissue and disrupt its crystallization.

The invention will be further described by reference to the following detailed examples.

EXAMPLES

An albumin-binding dye, Reactive Blue 2 and an albumin-binding dye/polymer conjugate, Blue Dextran, were applied to glutaraldehyde fixed heart valve tissue according to the present invention and were compared in calcification susceptibility tests to control heart valve tissue fixed with glutaraldehyde.

EXAMPLE 1

Porcine aortic valves were dissected and placed in HEPES buffered saline and refrigerated until used. The valves were treated in 0.2% glutaraldehyde solution in HEPES buffered saline for at least 72 hours and were stored in the same solution until further treatment.

The following test solution and treatment were provided to a portion of the glutaraldehyde-fixed valves:

Reactive Dye 2 (2.0 grams) was dissolved in 1000 ml water. Sodium chloride (20.2 grams) was added and the pH was brought to 8.35 by the addition of sodium carbonate. The valves were placed individually in 200 ml portions of this solution and incubated at 37 degrees C. for 72 hours. They were then rinsed in water for 72 hours. The valves were then stored in 70% reagent alcohol.

Leaflets from valves treated as set forth above with Reactive Dye 2 and untreated glutaraldehyde control samples were rinsed three times for 15 minutes in sterile saline solution. They were implanted subcutaneously in 3 week old rats. Explants were performed at 7, 14 and 21 days. Half the leaflet was placed in formaldehyde for histology (examination of the sample for calcium crystal formation) and half was placed in saline for atomic absorption measurement (a measure of total calcium in the sample). Three leaflets of each treatment were analyzed at each time period.

Figure 2:
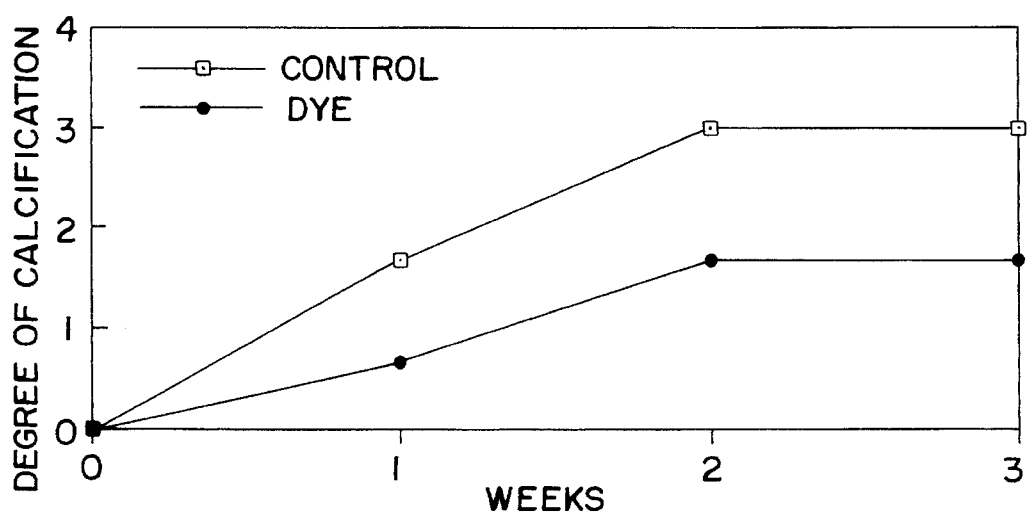
FIG. 2 is a graph comparing the calcification of control tissue (calcium crystallization) with that of dye-treated tissue according to the present invention as set forth in Example 1.

FIGS. 1 and 2 show the comparative results for atomic absorption and histology tests. While total calcium content in FIG. 1 was not found to be significantly different in the first two weeks, in the third week the calcium content of the dye-treated samples was found to be 32% lower than the control samples. Calcium crystal formation was found to have been suppressed substantially

EXAMPLE 2

Porcine aortic valves were dissected and placed in phosphate buffered saline (PBS) and refrigerated until used. The valves were treated in 0.2% glutaraldehyde in PBS for at least 72 hours and were stored in the same solution until further treatment.

The following test solution and treatment were provided to a portion of the glutaraldehyde-fixed valves:

Blue Dextran (6.0 grams) and 0.06 gram sodium periodate were mixed in 450 ml of deionized water for one hour. Five valves were placed in the solution for 24 hours. 500 ml of pH 5.0 potassium hydrogen phthalate solution were prepared and the valves were transferred to this solution. Sodium cyanoborohydride was added to make a 0.1M solution. The valves remained in the cyanoborohydride solution for 6 hours and were then rinsed in PBS and stored in 50% alcohol.

Leaflets from valves treated as set forth above with Blue Dextran and untreated glutaraldehyde control samples were rinsed three times for 15 minutes in sterile saline solution. They were then implanted subcutaneously in 3 week old rats. Explants were performed at 7, 14 and 21 days. Half of each leaflet was placed in formaldehyde for histology (examination of the sample for calcium crystal formation) and half was placed in saline for atomic absorption measurement (a measure of total calcium in the sample). Leaflets of each treatment were analyzed at each time period.

Figure 4:
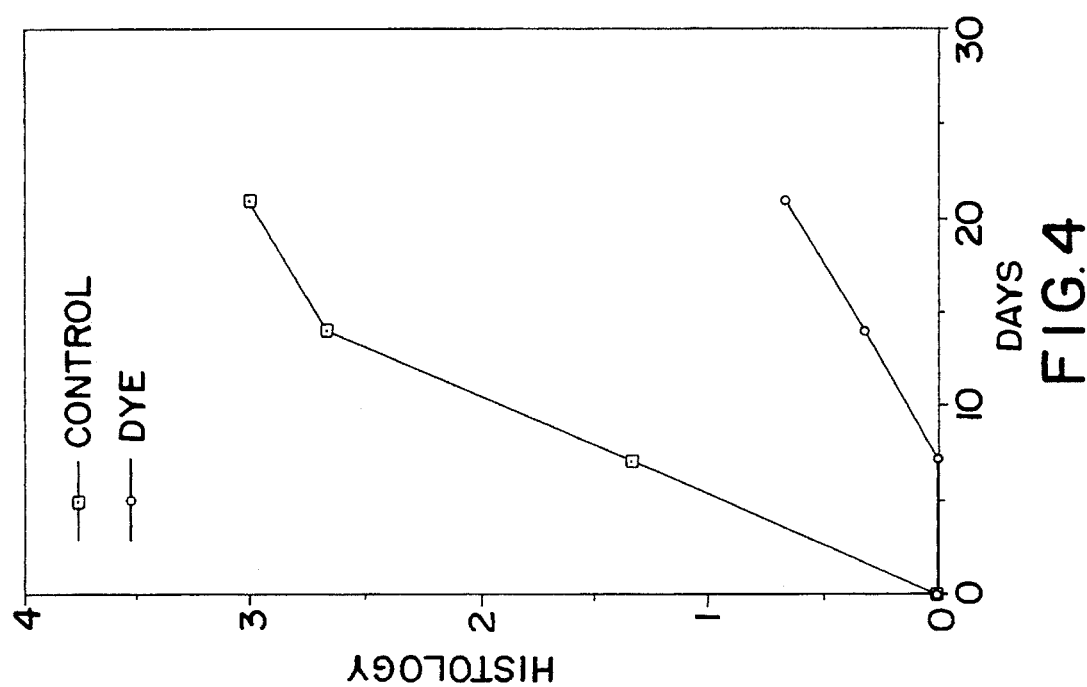
FIG. 4 is a graph comparing the calcification (calcium crystallization) of control tissue with that of dye-treated tissue according to the present invention as set forth in Example 2.
Figure 3:
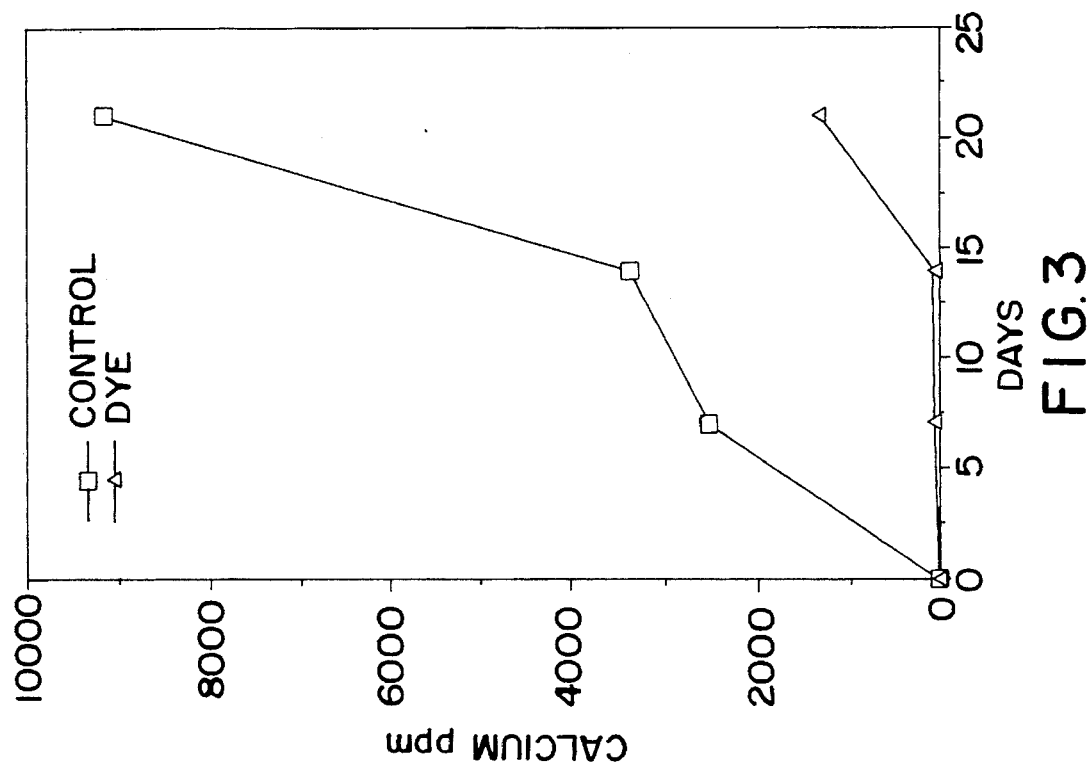
FIG. 3. is a graph comparing the calcification (calcium content) of control tissue with that of dye-treated tissue according to the present inventions set forth in Example 2.

FIGS. 3 and 4 show the comparative results for atomic absorption and histology tests. Total calcium content in FIG. 3 and calcium crystal formation in FIG. 4 were found to be substantially lower in the samples treated with blue dextran during each sampling period.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

What is claimed:

1. An implantable medical device comprising fixed tissue incorporating an amount of an albumin-binding dye effective to form a coating of endogenous albumin on said device when said device is in contact with a physiological fluid containing albumin.

2. The medical device of claim 1 wherein said albumin-binding dye comprises an aromatic albumin-binding dye.

3. The medical device of claim 2 wherein said aromatic albumin-binding dye comprises a diazo dye, a sulfonic acid dye, or the physiologically-acceptable salts thereof.

4. The medical device of claim 3 wherein said aromatic albumin-binding dye is selected from the group consisting of 1-Amino-4((4-((4-chloro-6-(( 3(or 4)-sulfophenyl)amino)-1,3, 5-triazin-2-yl)amino)-3-sulfophenyl)amino)-9,10-dihydro- 9,10-dioxo-2-anthracenesulfonic acid, 6.6'-(3,3'-Diamethyl (1,1'-biphenyl)- 4,4'diyl)bis(azo))bis(4-amino-5-hydroxy-1,3-naphthalene disulfonic acid) tetrasodium salt, 3,3'-(3,3'-Dimethyl(1,1'-biphenyl)-4,4'diyl)bis(-azo))bis(5-amino-4 hydroxy-2,7-naphthalenehydroxy disulfonic acid) tetrasodium salt, 4,4'-(3H-2,1-Benzoxathiol-3-ylidene) bis(2,6-dibromo-3-methylphenol)S,S-dioxide, 4,4'-(3H-2,1-benzoxathiol- 3-ylidene)bis(2-bromo-6-methylphenol) S,S-dioxide, 4-(((4-dimethylamino) phenyl)azo)benzene-sulfonic acid sodium salt, 2-(4'-hydroxyazobenzene)benzoic acid, Procion red H-E 3B and mixtures thereof.

5. The medical device of claim 1 wherein said fixed tissue comprises a conjugate comprising said albumin-binding dye and a physiologically-acceptable water-soluble polysaccharide.

6. The medical device of claim 5 wherein said polysaccharide comprises dextran.

7. The medical device of claim 6 wherein said albumin-binding dye comprises an aromatic albumin-binding dye.

8. The medical device of claim 7 wherein said aromatic albumin-binding dye comprises a diazo dye, a sulfonic acid dye, or the physiologically acceptable salts thereof.

9. The medical device of claim 8 wherein said aromatic albumin-binding dye is selected from the group consisting of 1-Amino-4((4-((4-chloro-6-(( 3(or 4)-sulfophenyl)amino)-1,3,5-triazin-2-yl)amino)-3-sulfophenyl)amino)-9,10-dihydro- 9,10-dioxo-2-anthracenesulfonic acid, 6,6'-(3,3'-Diamethyl (1,1'-biphenyl)- 4,4'diyl)bis(azo))bis(4-amino-5-hydroxy-1,3-naphthalene disulfonic acid) tetrasodium salt, 3,3'-(3,3'-Dimethyl(1,1'-biphenyl)-4,4'diyl)bis(azo))bis(5-amino4 hydroxy-2,7-naphthalene disulfonic acid) tetrasodium salt, 4,4'-(3H-2,1-Benzoxathiol-3-ylidene)bis( 2,6-dibromo-3-methylphenol)S,S-dioxide, 4,4'-(3H-2,1-benzoaxathiol- 3-ylidene)bis(2-bromo-6-methylphenol) S,S-dioxide, 4-(((4-dimethylamino phenyl)azo)benzene-sulfonic acid sodium salt, 2-(4'-hydroxyazobenzene)benzoic acid, Procion red H-E 3B, and mixtures thereof.

10. The medical device of claim 1 wherein said fixed tissue comprises an animal tissue fixed with glutaraldehyde.

11. The medical device of claim 1 wherein said fixed tissue is treated with a reducing agent.

12. The medical device of claim 11 wherein said reducing agent is cyanoborohydride.

13. The medical device of claim 1 wherein the endogenous albumin is human serum albumin.

14. The medical device of claim 1 wherein said medical device is a replacement heart valve and wherein said fixed tissue is the fixed tissue of the replacement heart valve.

15. The medical device of claim 1 wherein said medical device is a replacement blood vessel and said fixed tissue is the fixed tissue of the replacement blood vessel.

16. An implantable medical device comprising: a surface of fixed tissue and on the fixed tissue surface an amount of a conjugate comprising:
   a. an albumin-binding dye and
   b. a physiologically-acceptable water-soluble polymer, wherein said amount of the conjugate is effective to bind albumin to the fixed tissue surface of said medical device.

17. The medical device of claim 16 wherein said physiologically-acceptable water-soluble polymer comprises a polysaccharide.

18. The medical device of claim 17 wherein said polysaccharide comprises dextran.

19. The medical device of claim 16 wherein said conjugate is a coating.

20. The medical device of claim 16 wherein said conjugate is cast or molded into the medical device.

21. The medical device of claim 16 wherein said medical device is a replacement heart valve and wherein said fixed tissue is the fixed tissue of the replacement heart valve.

22. The medical device of claim 16 wherein said medical device is a replacement blood vessel and said fixed tissue is the fixed tissue of the replacement blood vessel.

23. The medical device of claim 16 wherein said fixed tissue has been fixed by treatment with glutaraldehyde.

24. The medical device of claim 16 wherein said fixed tissue has been treated with a reducing agent.

25. The medical device of claim 24 wherein the reducing agent is cyanoborohydride.

26. The medical device of claim 16 wherein said albumin-binding dye comprises an aromatic albumin-binding dye.

27. The medical device of claim 26 wherein said aromatic albumin-binding dye comprises a diazo dye, a sulfonic acid dye, or the physiologically acceptable salts thereof.

28. The medical device of claim 27 wherein said aromatic albumin-binding dye is selected from the group consisting of 1-Amino4((4-((4-chloro-6-(( 3(or 4)-sulfophenyl)amino)-1, 3,5-triazin-2-yl)amino)-3-sulfophenyl)amino)-9,10-dihydro- 9,10-dioxo-2-anthracenesulfonic acid, 6,6'-(3,3'-Diamethyl (1,1'-biphenyl)- 4,4'diyl)bis(azo))bis(4-amino-5-hydroxy-1,3-naphthalene disulfonic acid) tetrasodium salt, 3,3'-(3,3'-Dimethyl(1,1'-biphenyl)-4,4'diyl)bis(azo))bis(5-amino-4 hydroxy- 2,7-naphthalene disulfonic acid) tetrasodium salt, 4,4'-(3H-2,1-Benzoaxathiol-3-ylidene)bis( 2,6-dibromo-3-methylphenol)S,S-dioxide, 4,4'-(3H-2,1-benzoaxathiol- 3-ylidene)bis(2-bromo-6-methylphenol) S,S-dioxide, 4-(((4-dimethylamino) phenyl)azo)benzene-sulfonic acid sodium salt, 2-(4'-hydroxyazobenzene)benzoic acid, Procion red H-E 3B and mixtures thereof.

29. A method of increasing the albumin-binding ability of a implantable medical device comprising fixed tissue, said method comprising the step of:
   a. incorporating into said fixed tissue an amount of an albumin-binding dye; wherein the amount of the albumin-binding dye is effective to form a coating of endogenous albumin on a surface of said fixed tissue when the surface is in contact with a physiological fluid containing albumin.

30. The method of claim 29 wherein the albumin-binding dye comprises an aromatic albumin-binding dye.

31. The method of claim 30 wherein the aromatic albumin-binding dye comprises a diazo dye, a sulfonic acid dye, or the physiologically acceptable salts thereof.

32. The method of claim 31 wherein the aromatic albumin-binding dye is selected from the group consisting of 1-Amino-4((4-((4-chloro-6-((3(or 4)-sulfophenyl) amino)-1,3,5-triazin-2-yl)amino)-3-sulfophenyl)amino)-9,10-dihydro-9,10-dioxo- 2-anthracenesulfonic acid, 6,6'-(3,3'-Diamethyl (1,1'-biphenyl)- 4,4'diyl)bis(azo))bis(4-amino-5-hydroxy-1,3-naphthalene disulfonic acid) tetrasodium salt, 3,3'-(3,3'-Dimethyl(1,1'-biphenyl)-4,4'diyl)bis(azo))bis(5-amino-4 hydroxy- 2,7-naphthalene disulfonic acid) tetrasodium salt, 4,4'-(3H-2,1-Benzoxathiol-3-ylidene)bis( 2,6-dibromo-3-methylphenol)S,S-dioxide, 4,4'-(3H-2, 1benzoxathiol-3-ylidene)bis( 2-bromo-6-methylphenol) S,S-dioxide, 4-(((4-dimethylamino) phenyl)azo)benzene-sulfonic acid sodium salt, 2-(4'-hydroxyazobenzene) benzoic acid, Procion red H-E 3B, and mixtures thereof.

* * * * *